US010064977B2

(12) United States Patent
Jiang et al.

(10) Patent No.: US 10,064,977 B2
(45) Date of Patent: Sep. 4, 2018

(54) WET-PACK INTRAOCULAR LENS MATERIALS WITH HIGH REFRACTIVE INDEX

(71) Applicant: Novartis AG, Basel (CH)

(72) Inventors: Xuwei Jiang, Arlington, TX (US); Douglas Schlueter, Azle, TX (US); Walter Laredo, Fort Worth, TX (US)

(73) Assignee: Novartis AG, Basel (CH)

( * ) Notice: Subject to any disclaimer, the term of this patent is extended or adjusted under 35 U.S.C. 154(b) by 235 days.

(21) Appl. No.: 15/006,287

(22) Filed: Jan. 26, 2016

(65) Prior Publication Data

US 2016/0235886 A1 Aug. 18, 2016

Related U.S. Application Data

(60) Provisional application No. 62/116,724, filed on Feb. 16, 2015.

(51) Int. Cl.
| | |
|---|---|
| *C08F 220/30* | (2006.01) |
| *B29D 11/00* | (2006.01) |
| *A61L 27/16* | (2006.01) |
| *A61L 27/50* | (2006.01) |
| *A61F 2/16* | (2006.01) |
| *A61L 27/18* | (2006.01) |
| *A61L 27/26* | (2006.01) |

(52) U.S. Cl.
CPC ............. *A61L 27/16* (2013.01); *A61F 2/16* (2013.01); *A61L 27/18* (2013.01); *A61L 27/26* (2013.01); *A61L 27/50* (2013.01); *C08F 220/30* (2013.01); *A61L 2430/16* (2013.01); *C08F 2220/305* (2013.01)

(58) Field of Classification Search
USPC ........................................................ 526/312
See application file for complete search history.

(56) References Cited

U.S. PATENT DOCUMENTS

| | | | |
|---|---|---|---|
| 3,162,676 A | 12/1964 | Goldberg et al. | |
| 3,299,173 A | 1/1967 | Roselli | |
| 4,304,895 A | 12/1981 | Loshaek | |
| 4,528,311 A | 7/1985 | Beard et al. | |
| 4,612,358 A | 9/1986 | Besecke et al. | |
| 4,716,234 A | 12/1987 | Dunks et al. | |
| 4,834,750 A | 5/1989 | Gupta | |
| 5,290,892 A | 3/1994 | Namdaran et al. | |
| 5,331,073 A | 7/1994 | Weinschenk, III et al. | |
| 5,470,932 A | 11/1995 | Jinkerson | |
| 5,603,774 A | 2/1997 | LeBoeuf et al. | |
| 5,693,095 A | 12/1997 | Freeman et al. | |
| 5,922,821 A | 7/1999 | LeBoeuf et al. | |
| 6,140,438 A | 10/2000 | Ojio et al. | |
| 6,245,106 B1 | 6/2001 | Makker et al. | |
| 6,241,766 B1 | 7/2001 | Liao et al. | |
| 6,313,187 B2 | 11/2001 | LeBoeuf et al. | |
| 6,329,485 B1 | 12/2001 | Vanderbilt | |
| 6,353,069 B1 | 3/2002 | Freeman et al. | |
| 6,528,602 B1 | 3/2003 | Freeman et al. | |
| 6,653,422 B2 | 11/2003 | Freeman et al. | |
| 6,657,032 B2 | 12/2003 | Vanderbilt | |
| 6,703,466 B1 | 3/2004 | Karakelle et al. | |
| 6,780,899 B2 | 8/2004 | Liao et al. | |
| 6,806,337 B2 | 10/2004 | Schlueter et al. | |
| 6,852,793 B2 | 2/2005 | Salamone et al. | |
| 6,872,793 B1 | 3/2005 | Schlueter | |
| 7,585,900 B2 | 9/2009 | Cordova et al. | |
| 7,605,190 B2 | 10/2009 | Moszner et al. | |
| 7,652,076 B2 | 1/2010 | Schlueter et al. | |
| 7,714,039 B2 | 5/2010 | Cordova et al. | |
| 7,790,824 B2 | 9/2010 | Freeman | |
| 7,790,825 B2 | 9/2010 | Lehman et al. | |
| 7,799,845 B2 | 9/2010 | Schlueter | |
| 7,847,046 B2 | 12/2010 | Schlueter et al. | |
| 8,058,323 B2 | 11/2011 | Cordova et al. | |
| 8,153,703 B2 | 4/2012 | Laredo | |
| 8,232,326 B2 | 7/2012 | Laredo | |
| 8,362,177 B1 | 1/2013 | Lehman et al. | |
| 8,449,610 B2 | 5/2013 | Laredo et al. | |
| 8,466,209 B2 * | 6/2013 | Akinay | A61L 27/16 523/106 |
| 8,470,034 B2 | 6/2013 | Terrisse | |
| 8,557,892 B2 | 10/2013 | Laredo | |
| 2014/0180403 A1 | 6/2014 | Silvestrini et al. | |

FOREIGN PATENT DOCUMENTS

| | | | |
|---|---|---|---|
| WO | 99/08136 A1 | 2/1999 | |
| WO | 99/52570 A1 | 10/1999 | |
| WO | 99/53347 A1 | 10/1999 | |
| WO | 99/53348 A1 | 10/1999 | |

(Continued)

OTHER PUBLICATIONS

Sax et al.. Preparation and Infrared Absorption Spectra of Some Phenyl Ethers, J. Org. Chem, 1960, vol. 25, pp. 1590-1595.*
International Searching Authority, International Search Report and Written Opinion, PCT/US2016/014817, dated Apr. 6, 2016, 10 pages.
Full written translation of Hwang et al., Research of High Refractive and Flexible (Meth)acrylic Polymers for Soft Intraocular Lens by Designing Physical Properties of Polymer, published in Choson Minjujuui Inman Konghwaguk Kwahagwon Tongbo, Science and Technology Publishing (2009), 98(2), pp. 40-42.
Hwang et al., Research of High Refractive and Flexible (Meth)acrylic Polymers for Soft Intraocular Lens by Designing Physical Properties of Polymer, published in Choson Minjujuui Inman Konghwaguk Kwahagwon Tongbo, Science and Technology Publishing (2009), 98(2), pp. 40-42 (English Abstract).

(Continued)

*Primary Examiner* — Mark Kaucher
*Assistant Examiner* — Henry Hu
(74) *Attorney, Agent, or Firm* — Jian Zhou

(57) ABSTRACT

Intraocular lens materials are disclosed. They are soft and very deformable and have a high refractive index, and a high glistening resistance in fully hydrated state. They are particularly suitable for making wet-packed intraocular lenses (IOLs) which can be delivered through sub 2.0 mm incisions.

20 Claims, No Drawings

(56) References Cited

FOREIGN PATENT DOCUMENTS

| WO | WO-99/52570 | * | 10/1999 |
| WO | WO-99/53347 | * | 10/1999 |
| WO | 00/34804 A1 | | 6/2000 |

OTHER PUBLICATIONS

Sax et al., Preparation and Infrared Absorption Spectra of Some Phenyl Ethers, J. Org. Chem, 1960, vol. 25, pp. 1590-1595.

* cited by examiner

WET-PACK INTRAOCULAR LENS MATERIALS WITH HIGH REFRACTIVE INDEX

This application claims the benefits under 35 USC § 119 (e) of U.S. provisional application No. 62/116,724 filed Feb. 16, 2015, incorporated by reference in its entirety.

This invention is directed to soft wet-pack intraocular lens (IOL) materials. In particular, this invention relates to hydrophobic acrylic materials which, upon hydration, become soft and highly deformable with a hydrated refractive index of greater than 1.55 and minimal or no glistening.

BACKGROUND OF THE INVENTION

With advances in small-incision cataract surgery, increased emphasis has been placed on developing soft, foldable materials suitable for use in artificial lenses. In general, these materials fall into one of three categories: hydrogels, silicones, and acrylics.

In general, hydrogel materials have a relatively low refractive index, making them less desirable than other materials because of the thicker lens optic necessary to achieve a given refractive power. Conventional silicone materials generally have a higher refractive index than hydrogels, but tend to unfold explosively after being placed in the eye in a folded position. Explosive unfolding can potentially damage the corneal endothelium and/or rupture the natural lens capsule. Acrylic materials are desirable because they typically have a high refractive index and unfold more slowly or controllably than conventional silicone materials.

Acrylic materials suitable for intraocular lenses are generally soft and hydrophobic and have an equilibrium water content of less than 5% by weight. See, for example, those described in U.S. Pat. Nos. 4,834,750, 5,290,892, 5,331,073, 5,693,095, 5,922,821, 6,241,766, 6,245,106, 6,313,187, 6,353,069, 6,528,602, 6,653,422, 6,703,466, 6,780,899, 6,806,337, 6,872,793, 7,585,900, 7,652,076, 7,714,039, 7,790,824, 7,790,825, 7,799,845, 7,847,046, 8,058,323, 8,362,177, 8,466,209, 8,449,610, 8,557,892 (herein incorporated by references in their entireties). However, soft hydrophobic acrylic materials can be tacky. It is generally desirable to reduce the amount of surface tack in materials intended for use as a foldable intraocular lens. Tacky materials can be difficult to manufacture, handle, and unfold. Attempts have been made to reduce tackiness so that the lenses are easier to process or handle, easier to fold or deform, and have shorter unfolding times. For example, U.S. Pat. No. 5,603,774 discloses a plasma treatment process for reducing the tackiness of a soft acrylic material. U.S. Pat. Nos. 6,241,766; 6,245,106; 7,585,900; 7,714,039 and 8,362,177 disclose use of hydrophilic components or additives for reducing the tackiness of a soft acrylic material.

In addition, a soft hydrophobic acrylic material is susceptible to have glistenings (or microvacuoles) which are formed in vivo and can affect adversely the optical performance of intraocular lenses. Glistenings are tiny inclusions of water present within the matrix of an IOL material and are visible due to differences in refractive indices between the IOL material and water within the IOL material. It is reported that a polyethylene glycol (PEG)-containing polymerizable component (monomer and/or crosslinker) (U.S. Pat. Nos. 5,693,095, 6,353,069, and 8,449,610) can be used to improve glistening resistance of hydrophobic acrylic formulations. But, in order to minimize its adverse effects on the refractive index of acrylic materials, low amounts of PEG dimethacrylate or PEG mono-(meth)acrylate concentrations are often required. Addition of PEG dimethacrylates or PEG mono-(meth)acrylates also tends to decrease the modulus and tensile strength of the resulting copolymer.

U.S. Pat. No. 6,140,438 discloses glistening resistant soft hydrophobic acrylic materials obtained from a polymerizable composition comprising an aromatic ring-containing methacrylate monomer, a hydrophilic monomer (e.g., hydroxyethyl methacrylate) for improving glistering resistance, an alkyl (meth)acrylate for improving the flexibility and the shape restoration property of soft hydrophobic acrylic materials, and a crosslinkable monomer.

U.S. Pat. Nos. 6,329,485 and 6,657,032 disclose soft, foldable hydrogel lens materials which have a water content of approximately 5 to 30 percent by weight and are made from a composition comprising two principal monomers, one aromatic high refractive index monomer and one hydrophilic (meth)acrylate monomer (e.g., hydroxyethyl methacrylate) in an amount greater than that of the aromatic high refractive index monomer.

U.S. Pat. No. 6,852,793 discloses polymeric compositions which have a water content from 4.5 to 15 percent by weight, a relatively high refractive index of approximately 1.45 or greater, and a relatively high elongation of approximately 80 percent or greater and which produced through the polymerization of one or more copolymers with one or more hydrophilic monomers (preferably N,N-dimethylacrylamide) and optionally one or more aromatic-based monomers, hydrophobic monomers or a combination thereof.

SUMMARY OF THE INVENTION

The present invention provides soft, hydrophobic acrylic materials suitable for making wet-packed IOLs which can be delivered through sub 2.0 mm incisions.

The present invention is partly based on the finding that poly(phenyl ether)-containing monomers can be combined with a hydroxyl-containing methacrylate or acrylate or a hydrophilic methacrylamide or acrylamide monomer to prepare a polymeric material which, upon hydration, become soft and highly-deformable (an elongation at break or maximum strain of greater than 100%, a Young's modulus of about 80 MPa or less, a 100% secant modulus of less than 6.0 MPa) and has a refractive index of greater than 1.55, an equilibrium water content (EWC) of less than 5.0% by weight, and a high resistance against glistenings (no bright field glistenings and minimal dark field glistenings) induced by temperature change. Because of their relatively-rigid forms in dry state at room temperature, manufacturing and handling problems associated with the surface tackiness of a hydrophobic acrylic material can be significantly reduced or eliminated. With high glistening resistance, high refractive index and high softness and deformability, the subject materials are suitable for wet-pack IOLs for microincision applications.

DETAILED DESCRIPTION OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art.

"About" as used herein means that a number referred to as "about" comprises the recited number plus or minus 1-10% of that recited number.

"Optional" or "optionally" means that the subsequently described event or circumstance can or cannot occur, and that the description includes instances where the event or circumstance occurs and instances where it does not.

Unless indicated otherwise, all component amounts are presented on a % (w/w) basis ("wt. %").

The term "alkyl" refers to a monovalent radical obtained by removing a hydrogen atom from a linear or branched alkane compound. An alkyl group (radical) forms one bond with one other group in an organic compound.

The term "alkylene divalent group" or "alkylene diradical" or "alkyl diradical" interchangeably refers to a divalent radical obtained by removing one hydrogen atom from an alkyl. An alkylene divalent group forms two bonds with other groups in an organic compound.

The term "alkoxy" or "alkoxyl" refers to a monovalent radical obtained by removing the hydrogen atom from the hydroxyl group of a linear or branched alkyl alcohol. An alkoxy group (radical) forms one bond with one other group in an organic compound.

In this application, the term "substituted" in reference to an alkyl diradical or an alkyl radical means that the alkyl diradical or the alkyl radical comprises at least one substituent which replaces one hydrogen atom of the alkyl diradical or the alkyl radical and is selected from the group consisting of hydroxy (—OH), carboxy (—COOH), —NH$_2$, sulfhydryl (—SH), $C_1$-$C_4$ alkyl, $C_1$-$C_4$ alkoxy, $C_1$-$C_4$ alkylthio (alkyl sulfide), $C_1$-$C_4$ acylamino, $C_1$-$C_4$ alkylamino, di-$C_1$-$C_4$ alkylamino, halogen atom (Br or Cl), and combinations thereof.

In general, the invention is directed to intraocular lens materials which are soft and very deformable and have a high refractive index, a high glistening resistance, and a low aging-related surface light scattering, in a fully hydrated state.

An intraocular lens material of the invention is a polymerization product of a polymerizable composition comprising:

(a) from about 10% to about 30% (preferably from about 15% to about 25%, more preferably from about 18% to about 22%) by weight of a hydrophilic monomer relative to the total amount of all polymerizable components, wherein the hydrophilic monomer is hydroxyethylmethacrylate, hydroxyethylacrylate, N-hydroxyethylmethacrylamide, N-hydroxyethylacrylamide, N,N-dimethylacrylamide, N,N-dimethylmethacrylamide, or a combination thereof, (b) from about 20% to about 85% (preferably from about 25% to about 75%, more preferably from about 30% to about 65%) by weight of one or more poly(phenyl ether)-containing monomers of formula (I) relative to the total amount of all polymerizable components

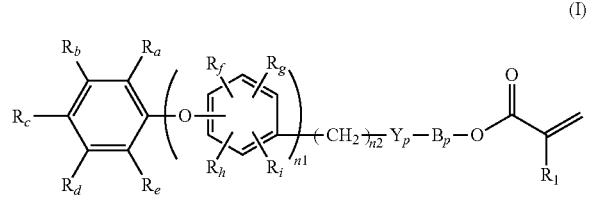

(I)

wherein:
$R_1$ is H or $CH_3$;
$R_a$, $R_b$, $R_c$, $R_d$, $R_e$, $R_f$, $R_g$, $R_h$, and $R_i$ independent of one another are H, $C_1$-$C_{12}$ alkyl, or $C_1$-$C_{12}$ alkoxy (preferably all are H);
$B_p$ is a direct bond, $(CH_2)_{m1}$, or $(OCH_2CH_2)_{m2}$, in which m1 is 2-6 and m2 is 1-10;
n1 is an integer from 1 to 9 (preferably from 2 to 6, more preferably from 2 to 4, even more preferably 2 or 3);
n2 is an integer from 0 to 6 (preferably from 0 to 4);
$Y_p$ is a direct bond, O, S, OC(=O)NH, NHC(=O)NH, or NR' in which R' is H, $C_1$-$C_{10}$ alkyl, $C_6H_5$, or $CH_2C_6H_5$, (c) from 0 to about 50% by weight (preferably from about 10% to about 45% by weight, more preferably from about 20% to about 40% by weight) of one or more aryl acrylic monomers of formula (II) relative to the total amount of all polymerizable components

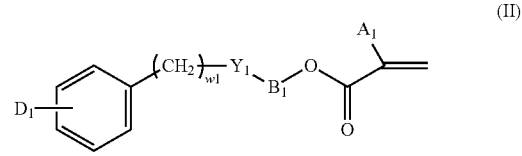

(II)

wherein $A_1$ is H or $CH_3$ (preferably H); $B_1$ is $(CH_2)_{m1}$ or $[O(CH_2)_2]_{z1}$ in which m1 is 2-6 and z1 is 1-10; $Y_1$ is a direct bond, O, S, or NR' in which R' is H, $CH_3$, $C_nH_{2n'+1}$ in which n'=1-10, iso-$OC_3H_7$, $C_6H_5$, or $CH_2C_6H_5$; W1 is 0-6, provided that m1+w1≤8; and $D_1$ is H, Cl, Br, $C_1$-$C_4$ alkyl, $C_1$-$C_4$ alkoxy, $C_6H_5$, or $CH_2C_6H_5$, and (d) one or more polymerizable crosslinking agents, wherein the listed components and any additional polymerizable components add up to 100% by weight, wherein the intraocular lens material in a fully-hydrated state has: a glass transition temperature of less than 22° C. (preferably less than 17° C. or less, more preferably less than 12° C.), a refractive index of 1.55 or greater measured at 589 nm and at room temperature (23±2° C.), an equilibrium water content of less than 5.0% (preferably from about 1% to about 4.5%, more preferably from about 1.5% to about 4.0%) by weight at a temperature of from 16° C. to 45° C., a Young's modulus of less than 80 MPa (preferably from about 1 MPa to about 60 MPa, more preferably from about 2.5 MPa to about 40 MPa, even more preferably from about 5 MPa to 20 MPa), an elongation of at least 100% (preferably at least 110%, more preferably at least 120%, even more preferably at least 130%, most preferably from 130% to 300%), a 100% secant modulus of less than 6.0 MPa (preferably about 4.5 MPa or less, more preferably about 3.0 MPa or less), and a glistening resistance characterized by having no bright field microvacuoles and about 10 or less microvacuoles per viewing screen. Preferably, the intraocular lens material is substantially free or completely free of age-related degradation as measured by low surface light scattering of less than 30 CCT units (computer-compatible-tape units) after 10-years accelerated aging (90° C., 81 days in a Balanced Salt Solution, BSS, from Alcon). By minimizing or eliminating this age-related degradation issue, the subject materials are suitable for making wet-packed, glistening resistant, higher refractive index IOLs for microincision applications.

In accordance with the invention, a device material of the invention should have a glass transition temperature of less than 22° C. (preferably less than 17° C., more preferably less than 12° C.) in a fully hydrated state.

For use in IOLs, the materials in a fully-hydrated state of the present invention preferably exhibit sufficient strength, low stiffness, and low 100% secant modulus to allow devices made of them to be soft and highly deformable for microincision applications. Thus, an intraocular lens material of the present invention will have: an elongation (% strain at break) of at least 100% (preferably at least 110%, more preferably at least 120%, even more preferably at least 130%, most preferably from 130% to 300%); a Young's modulus of less than 80 MPa (preferably from about 1 MPa to about 60 MPa, more preferably from about 2.5 MPa to about 40 MPa, even more preferably from about 5 MPa to 20 MPa); and a 100% secant modulus of less than 6.0 MPa (preferably about 4.5 MPa or less, more preferably about 3.0 MPa or less). With such properties intraocular lenses made of such a material generally will not crack, tear or split when folded. Elongation of hydrated polymer samples is determined on dumbbell shaped tension test specimens with a 20 mm total length, length in the grip area of 4.88 mm, overall width of 2.49 mm, 0.833 mm width of the narrow section, a fillet radius of 8.83 mm, and a thickness of 0.9 mm. Testing is performed on hydrated samples at ambient conditions (23±2° C., 50±5% relative humidity) using an Instron Material Tester (Model No. 4442 or equivalent) with a 50 Newton load cell. The grip distance is set at 14 mm and a crosshead speed is set at 500 mm/minute and the sample is pulled until failure. The elongation (strain) is reported as a fraction of the displacement at failure to the original grip distance. The strain at break (or maximum strain) is reported as a fraction of the displacement at failure to the original grip distance. Stress at break is calculated at the maximum load for the sample, typically the load when the sample breaks, assuming that the initial area remains constant. The Young's modulus is calculated from the instantaneous slope of the stress-strain curve in the linear elastic region. The 50% secant modulus is calculated as the slope of a straight line drawn on the stress-strain curve between 0% strain and 50% strain. The 100% secant modulus is calculated as the slope of a straight line drawn on the stress-strain curve between 0% strain and 100% strain. Since materials to be tested are essentially soft elastomers, loading them into the Instron machine tends to make them buckle. To remove the slack in the material sample a pre-load is placed upon the sample. This helps to reduce the slack and provide a more consistent reading. Once the sample is pre-loaded to a desired value (typically 0.03 to 0.05 N) the strain is set to zero and the test is begun.

An intraocular lens material of the present invention has an equilibrium water content of less than 5.0% (preferably from about 1% to about 4.5%, more preferably from about 1.5% to about 4.0%) by weight across the temperature range of 16-45° C. The device materials are preferably resistant to glistenings such that when equilibrated in water at 45° C. and subsequently allowed to cool to ambient temperature (approximately 22° C.) should produce no BF microvacuoles and at most 10 DF microvacuoles as detected by microscopic examination.

The polymerizable composition for making an intraocular lens material of the invention comprises from about 10% to about 30% (preferably from about 15% to about 25%, more preferably from about 18% to about 22%) by weight of a hydrophilic monomer, which is hydroxyethylmethacrylate, hydroxyethylacrylate, N-hydroxyethylmethacrylamide, N-hydroxyethylacrylamide, N,N-dimethylacrylamide, N,N-dimethylmethacrylamide, or a combination thereof (preferably hydroxyethylmethacrylate, hydroxyethylacrylate, N-hydroxyethylacrylamide, N,N-dimethylacrylamide, or a combination thereof, more preferably hydroxyethylmethacrylate, hydroxyethylacrylate, or a combination thereof). It is believed that hydroxyethyl methacrylate may be advantageously used to reduce surface light scattering after years of accelerating aging in a balanced salt solution (at 90° C. for 81 days).

Poly(phenyl ether)-containing monomers of formula (I) can be prepared from monofunctional polyphenyl ethers (i.e., ones with one functional group such as hydroxyl, amino, or carboxyl groups). Generally, a monofunctional OH-terminated poly(phenyl ether) is reacted with a (meth) acrylic acid derivative (such as acryloyl chloride, methacryloyl chloride, methacrylic anhydride, or an isocyanatoalkyl acrylate or methacrylate) under coupling reaction conditions known to a person skilled in the art. Mono-amine and mono-carboxylic acid terminated polyphenyl ethers are functionalized in a similar manner using suitable (meth) acrylic acid derivatives. Monofunctional terminated polyphenyl ethers can be prepared according to procedures described in literature (*J. Org. Chem.*, 1960, 25 (9), pp 1590-1595, herein incorporated by reference in its entirety).

In a preferred embodiment, the poly(phenyl ether)-containing monomer in the polymerizable composition is represented by formula (I) in which n1 is 2 or 3. Examples of such preferred poly(phenyl ether)-containing monomers include without limitation:

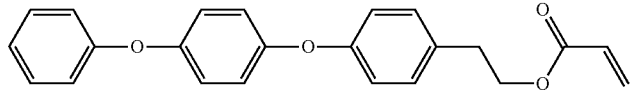

P3E2EA

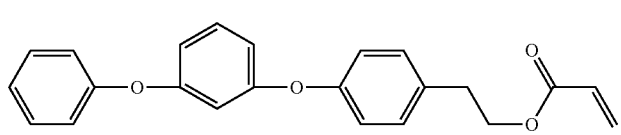

P3E2EA

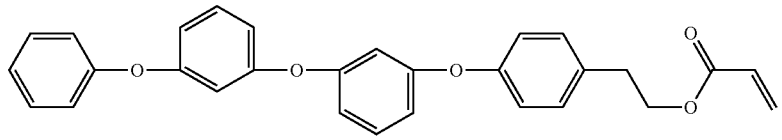

P4E3EA

-continued

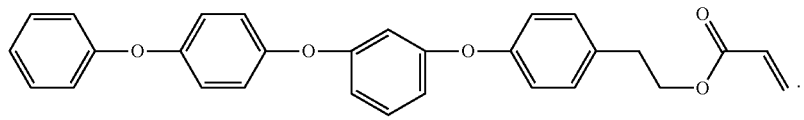

P4E3EA

Aryl acrylic monomers of formula (II) can be made by methods known in the art. For example, the conjugate alcohol of the desired monomer can be combined in a reaction vessel with methyl acrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding acrylic acid to the conjugate alcohol and catalyzing with a carbodiimide or mixing the conjugate alcohol with acryloyl chloride and a base such as pyridine or triethylamine.

Suitable aryl acrylic monomers of formula (II) include, but are not limited to: 2-ethylphenoxy acrylate; 2-ethylphenoxy methacrylate; phenyl acrylate; phenyl methacrylate; benzyl acrylate; benzyl methacrylate; 2-phenylethyl acrylate; 2-phenylethyl methacrylate; 3-phenylpropyl acrylate; 3-phenylpropyl methacrylate; 4-phenylbutyl acrylate; 4-phenylbutyl methacrylate; 4-methylphenyl acrylate; 4-methylphenyl methacrylate; 4-methylbenzyl acrylate; 4-methylbenzyl methacrylate; 2-2-methylphenylethyl acrylate; 2,2-methylphenylethyl methacrylate; 2,3-methylphenylethyl acrylate; 2,3-methylphenylethyl methacrylate; 2,4-methylphenylethyl acrylate; 2,4-methylphenylethyl methacrylate; 2-(4-propylphenyl)ethyl acrylate; 2-(4-propylphenyl)ethyl methacrylate; 2-(4-(1-methylethyl)phenyl) ethyl acrylate; 2-(4-(1-methylethyl)phenyl)ethyl methacrylate; 2-(4-methoxyphenyl)ethyl acrylate; 2-(4-methoxyphenyl)ethyl methacrylate; 2-(4-cyclohexylphenyl) ethyl acrylate; 2-(4-cyclohexylphenyl)ethyl methacrylate; 2-(2-chlorophenyl)ethyl acrylate; 2-(2-chlorophenyl)ethyl methacrylate; 2-(3-chlorophenyl)ethyl acrylate; 2-(3-chlorophenyl)ethyl methacrylate; 2-(4-chlorophenyl)ethyl acrylate; 2-(4-chlorophenyl)ethyl methacrylate; 2-(4-bromophenyl)ethyl acrylate; 2-(4-bromophenyl)ethyl methacrylate; 2-(3-phenylphenyl)ethyl acrylate; 2-(3-phenylphenyl)ethyl methacrylate; 2-(4-phenylphenyl)ethyl acrylate; 2-(4-phenylphenyl)ethyl methacrylate; 2-(4-benzylphenyl)ethyl acrylate; 2-(4-benzylphenyl)ethyl methacrylate; 2-(phenylthio)ethyl acrylate; 2-(phenylthio)ethyl methacrylate; 2-benzyloxyethyl acrylate; 3-benzyloxypropyl acrylate; 2-benzyloxyethyl methacrylate; 3-benzyloxypropyl methacrylate; 2-[2-(benzyloxy)ethoxy]ethyl acrylate; 2-[2-(benzyloxy) ethoxy]ethyl methacrylate; or combinations thereof.

Preferred aryl acrylic monomers of formula (II) are those wherein $B_1$ is $OCH_2CH_2$, $(OCH_2CH_2)_2$, $(OCH_2CH_2)_3$, or $(CH_2)_{m1}$ in which m1 is 2-5, $Y_1$ is a direct bond or O, w1 is 0 or 1, and $D_1$ is H. Most preferred are 2-phenylethyl acrylate; 3-phenylpropyl acrylate; 4-phenylbutyl acrylate; 5-phenylpentyl acrylate; 2-benzyloxyethyl acrylate; 3-benzyloxypropyl acrylate; 2-[2-(benzyloxy)ethoxy]ethyl acrylate; and their corresponding methacrylates.

The polymerizable composition for making an intraocular lens material of the invention further comprises one or more polymerizable cross-linking agents. The cross-linking agents may be any terminally ethylenically unsaturated compound having two or more ethylenically unsaturated groups. Suitable cross-linking agents include, for example: ethylene glycol dimethacrylate; diethylene glycol dimethacrylate; triethylene glycol dimethacrylate, tetraethylene glycol dimethacrylate, allyl methacrylate; 1,3-propanediol dimethacrylate; 2,3-propanediol dimethacrylate; 1,6-hexanediol dimethacrylate; 1,4-butanediol dimethacrylate; ethylene glycol diacrylate; diethylene glycol diacrylate; triethylene glycol diacrylate, tetraethylene glycol diacrylate, allyl acrylate; 1,3-propanediol diacrylate; 2,3-propanediol diacrylate; 1,6-hexanediol diacrylate; 1,4-butanediol diacrylate; N,N'-hexamethylene bisacrylamide; N,N'-hexamethylene bismethacrylamide; N,N'-dihydroxyethylene bisacrylamide; N,N'-dihydroxyethylene bismethacrylamide; N,N'-methylene bisacrylamide; N,N'-methylene bismethacrylamide; $CH_2=C(CH_3)C(=O)O-(CH_2CH_2O)_p-C(=O)C(=O)C(CH_3)=CH_2$ where p=1-50; $CH_2=CHC(=O)O-(CH_2CH_2O)_p-C(=O)CH=CH_2$ where p=1-50; $CH_2=C(CH_3)C(=O)O(CH_2)_tO-C(=O)C(CH_3)=CH_2$ where t=3-20; and $CH_2=CHC(=O)O(CH_2)_tO-C(=O)CH=CH_2$ where t=3-20. A preferred cross-linking monomer is 1,6-hexanediol diacrylate, 1,4-butanediol diacrylate, or N,N'-hexamethylene bisacrylamide.

Generally, the total amount of the cross-linking components is from about 1.0% to about 4.0% by weight, preferably from about 1.2% to about 3.0% by weight, even more preferably from about 1.5% to about 2.5% by weight.

The polymerizable composition for making an intraocular lens material of the invention may further comprise a poly(ethylene glycol)-containing (PEG-containing) polymerizable component.

In addition to the polymerizable components described above, the intraocular lens materials of the present invention may also contain other ingredients, including, but not limited to, polymerizable UV-absorbers (or UV-absorbing agents), polymerizable colored dyes, siloxane monomers, and combinations thereof.

A polymerizable ultraviolet (UV) absorbing agent can also be included in the materials of the present invention. The polymerizable UV-absorbing agent can be any compound which absorbs UV light (i.e., light having a wavelength shorter than about 380 nm) and optionally high-energy-violet-light (HEVL) (i.e., light having a wavelength between 380 nm and 440 nm), but does not absorb any substantial amount of visible light having a wavelength greater than 440 nm. The UV-absorbing compound is incorporated into the monomer mixture and is entrapped in the polymer matrix when the monomer mixture is polymerized. Any suitable polymerizable UV-absorbing agents can be used in the invention. A polymerizable UV-absorbing agent used in the invention comprises a benzophenone-moiety or preferably a benzotriazole-moiety. Polymerizable benzophenone-containing UV-absorbing agents can be prepared according to procedures described in U.S. Pat. Nos. 3,162,676 and 4,304,895 (herein incorporated by reference in their entirety) or can be obtained from commercial suppliers. Polymerizable benzotriazole-containing UV-absorbing agents can be prepared according to procedures described in U.S. Pat. Nos. 3,299,173, 4,612,358, 4,716,234, 4,528,311, 8,153,703, and U.S. Pat. No. 8,232,326 (herein incorporated by reference in their entireties) or can be obtained from commercial suppliers.

Examples of preferred polymerizable benzophenone-containing UV-absorbing agents include without limitation 2-hydroxy-4-acryloxy alkoxy benzophenone, 2-hydroxy-4-methacryloxy alkoxy benzophenone, allyl-2-hydroxybenzophenone, 4-acryloylethoxy-2-hydroxybenzophenone (UV2), 2-hydroxy-4-methacryloyloxybenzophenone (UV7), or combinations thereof.

Examples of preferred polymerizable benzotriazole-containing UV-absorbing and UV/HEVL-absorbing agents include without limitation: 2-(2-hydroxy-5-vinylphenyl)-2H-benzotriazole, 2-(2-hydroxy-5-acryloxyphenyl)-2H-benzotriazole, 2-(2-hydroxy-3-methacrylamido methyl-5-tert octylphenyl)benzotriazole, 2-(2'-hydroxy-5'-methacrylamidophenyl)-5-chlorobenzotriazole, 2-(2'-hydroxy-5'-methacrylamidophenyl)-5-methoxybenzotriazole, 2-(2'-hydroxy-5'-methacryloxypropyl-3'-t-butyl-phenyl)-5-chlorobenzotriazole, 2-(2'-hydroxy-5'-methacryloxypropylphenyl)benzotriazole, 2-hydroxy-5-methoxy-3-(5-(trifluoromethyl)-2H-benzo[d][1,2,3]triazol-2-yl)benzyl methacrylate (WL-1), 2-hydroxy-5-methoxy-3-(5-methoxy-2H-benzo[d][1,2,3]triazol-2-yl)benzyl methacrylate (WL-5), 3-(5-fluoro-2H-benzo[d][1,2,3]triazol-2-yl)-2-hydroxy-5-methoxybenzyl methacrylate (WL-2), 3-(2H-benzo[d][1,2,3]triazol-2-yl)-2-hydroxy-5-methoxybenzyl methacrylate (WL-3), 3-(5-chloro-2H-benzo[d][1,2,3]triazol-2-yl)-2-hydroxy-5-methoxybenzyl methacrylate (WL-4), 2-hydroxy-5-methoxy-3-(5-methyl-2H-benzo[d][1,2,3]triazol-2-yl)benzyl methacrylate (WL-6), 2-hydroxy-5-methyl-3-(5-(trifluoromethyl)-2H-benzo[d][1,2,3]triazol-2-yl)benzyl methacrylate (WL-7), 4-allyl-2-(5-chloro-2H-benzo[d][1,2,3]triazol-2-yl)-6-methoxyphenol (WL-8), 2-{2'-Hydroxy-3'-tert-5'[3"-(4"-vinylbenzyloxy)propoxy]phenyl}-5-methoxy-2H-benzotriazole, phenol, 2-(5-chloro-2H-benzotriazol-2-yl)-6-(1,1-dimethylethyl)-4-ethenyl-(UVAM), 2-(2'-hydroxy-5'-methacryloxyethylphenyl)benzotriazole (2-Propenoic acid, 2-methyl-, 2-[3-(2H-benzotriazol-2-yl)-4-hydroxyphenyl] ethyl ester, Norbloc), 2-{2'-Hydroxy-3'-tert-butyl-5'-[3'-methacryloyloxypropoxy]phenyl}-5-methoxy-2H-benzotriazole (UV13), 2-[2'-Hydroxy-3'-tert-butyl-5'-(3'-acryloyloxypropoxy)phenyl]-5-trifluoromethyl-2H-benzotriazole ($CF_3$—UV13), 2-(2'-hydroxy-5-methacrylamidophenyl)-5-methoxybenzotriazole (UV6), 2-(3-allyl-2-hydroxy-5-methylphenyl)-2H-benzotriazole (UV9), 2-(2-Hydroxy-3-methallyl-5-methylphenyl)-2H-benzotriazole (UV12), 2-3'-t-butyl-2'-hydroxy-5'-(38"-dimethylvinylsilylpropoxy)-2'-hydroxyphenyl)-5-methoxybenzotriazole (UV15), 2-(2'-hydroxy-5'-methacryloylpropyl-3'-tert-butyl-phenyl)-5-methoxy-2H-benzotriazole (UV16), 2-(2'-hydroxy-5'-acryloylpropyl-3'-tert-butyl-phenyl)-5-methoxy-2H-benzotriazole (UV16A), 2-Methylacrylic acid 3-[3-tert-butyl-5-(5-chlorobenzotriazol-2-yl)-4-hydroxyphenyl]-propyl ester (16-100, CAS#96478-15-8), 2-(3-(tert-butyl)-4-hydroxy-5-(5-methoxy-2H-benzo[d][1,2,3]triazol-2-yl)phenoxy)ethyl methacrylate (16-102); Phenol, 2-(5-chloro-2H-benzotriazol-2-yl)-6-methoxy-4-(2-propen-1-yl) (CAS#1260141-20-5); 2-[2-Hydroxy-5-[3-(methacryloyloxy)propyl]-3-tert-butylphenyl]-5-chloro-2H-benzotriazole; Phenol, 2-(5-ethenyl-1H-benzotriazol-2-yl)-4-methyl-, homopolymer (9CI) (CAS#83063-87-0).

More preferably, a polymerizable UV-absorbing agent is 2-(2H-benzo[d][1,2,3]triazol-2-yl)-4-methyl-6-(2-methylallyl)phenol (oMTP), 3-[3-tert-butyl-4-hydroxy-5-(5-methoxy-2-benz[d][1,2,3]triazol-2-yl)phenoxy]propyl methacrylate (UV13), and 2-[3-(2H-benzotriazol-2-yl)-4-hydroxyphenyl]ethyl methacrylate (Norbloc 7966), or combinations thereof.

In addition to ultraviolet absorbing materials, ophthalmic devices made of the copolymers of the present invention may include colored dyes, such as the yellow dyes disclosed in U.S. Pat. No. 5,470,932.

Intraocular lens materials of this invention are prepared by conventional polymerization methods. For example, a mixture of a hydrophilic monomer, one or more monomers of formula (I), one or more monomers of formula (II), and a cross-linking agent in the desired proportions, together with any other polymerizable components, such as a UV absorber, yellow dye, and a conventional thermal initiator (or a photoiniator) is prepared. The mixture can then be introduced into a mold of desired shape, and the polymerization carried out thermally (i.e., by heating) or photochemically (i.e., by actinic radiation, e.g., UV radiation and/or visible radiation) to activate the initiator. Preferably, the mixture is cured thermally. It is found that photocuring may results in higher bulk haze.

Examples of suitable thermal initiators include: but are not limited to, azonitriles, such as 2,2'-azobis (2,4-dimethylpentanenitrile), 2,2'-azobis (2-methylpropanenitrile), 2,2'-azobis (2-methylbutanenitrile), 2,2'-azobis(isobutyronitrile) (AIBN); peroxides, such as benzoyl peroxide; peroxycarbonates, such as bis-(4-t-butylcyclohexyl) peroxydicarbonate, and the like. A preferred initiator is AIBN, more preferably Luperox A98 (dibenzoyl peroxide). Luperox A98 is found to be better than AIBN especially for preventing pre-release without wafer plasma treatment.

Where the polymerization is carried out photochemically, a mold should be transparent to actinic radiation of a wavelength capable of initiating polymerization. Conventional photoinitiator compounds, e.g., a benzophenone-type or bisacylphosphine oxide (BAPO) photoinitiator, can also be introduced to facilitate the polymerization. Suitable photoinitiators are benzoin methyl ether, diethoxyacetophenone, a benzoylphosphine oxide, 1-hydroxycyclohexyl phenyl ketone, Darocur and Irgacur types photoinitiators (preferably Darocur 1173®, Darocur 2959® and Irgacure 819®), and Germanium-based Norrish Type I photoinitiators which are capable of initiating a free-radical polymerization under irradiation with a light source including a light in the region of about 400 to about 550 nm. Examples of benzoylphosphine initiators include 2,4,6-trimethylbenzoyldiphenylophosphine oxide; bis-(2,6-dichlorobenzoyl)-4-N-propylphenylphosphine oxide; and bis-(2,6-dichlorobenzoyl)-4-N-butylphenylphosphine oxide. Examples of Germanium-based Norrish Type I photoinitiators are acylgermanium compounds described in U.S. Pat. No. 7,605,190 (herein incorporated by reference in its entirety).

Once the intraocular lens materials of the present invention have been cured, they are extracted in a suitable solvent to remove as much of the unreacted components of the materials as possible. Examples of suitable solvents include acetone, methanol, and cyclohexane. A preferred solvent for extraction is acetone.

IOLs constructed of the disclosed intraocular lens materials can be of any design capable of being rolled or folded into a small cross section that can fit through a relatively smaller incision. For example, the IOLs can be of what is known as a one piece or multipiece design. Typically, an IOL comprises an optic and at least one haptic. The optic is that portion which serves as the lens and the haptics are attached to the optic and are like arms which hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the intraocular lens materials of the present invention are also suitable for use in other devices, including contact lenses, keratoprostheses, intracorneal lenses, corneal inlays or rings, and glaucoma filtration devices.

These IOL materials can be used to form intraocular lenses with low surface tack and high refractive indexes. Lenses made of these materials are flexible and transparent, can be inserted into the eye through a relatively small incision, and recover their original shape after having been inserted.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together, as illustrated below:

1. A polymeric intraocular lens material, which is polymerization product of a polymerizable composition comprising
   (a) from about 10% to about 30% by weight of a hydrophilic monomer relative to the total amount of all polymerizable components, wherein the hydrophilic monomer is hydroxyethylmethacrylate, hydroxyethylacrylate, N-hydroxyethylmethacrylamide, N-hydroxyethylacrylamide, N,N-dimethylacrylamide, N,N-dimethylmethacrylamide, or a combination thereof,
   (b) from about 20% to about 85% by weight of one or more poly(phenyl ether)-containing monomers of formula (I) relative to the total amount of all polymerizable components

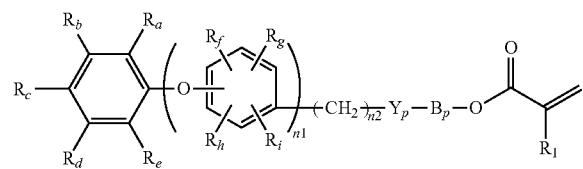

(I)

wherein:
   $R_1$ is H or $CH_3$;
   $R_a$, $R_b$, $R_c$, $R_d$, $R_e$, $R_f$, $R_g$, $R_h$, and $R_i$ independent of one another are H, $C_1$-$C_{12}$ alkyl, or $C_1$-$C_{12}$ alkoxy (preferably all are H);
   $B_p$ is a direct bond, $(CH_2)_{m1}$, or $(OCH_2CH_2)_{m2}$, in which m1 is 2-6 and m2 is 1-10;
   n1 is an integer from 1 to 9 (preferably from 2 to 6, more preferably from 2 to 4, even more preferably 2 or 3);
   n2 is an integer from 0 to 6 (preferably from 0 to 4);
   $Y_p$ is a direct bond, O, S, OC(=O)NH, NHC(=O)NH, or NR' in which R' is H, $C_1$-$C_{10}$ alkyl, $C_6H_5$, or $CH_2C_6H_5$,
   (c) from 0 to about 50% by weight of one or more aryl acrylic monomers of formula (II) relative to the total amount of all polymerizable components

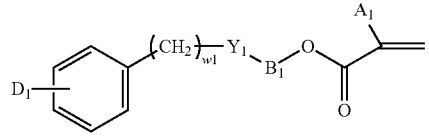

(II)

wherein $A_1$ is H or $CH_3$ (preferably H); $B_1$ is $(CH_2)_{m1}$ or $[O(CH_2)_2]_{z1}$ in which m1 is 2-6 and z1 is 1-10; $Y_1$ is a direct bond, O, S, or NR' in which R' is H, $CH_3$, $C_{n'}H_{2n'+1}$ in which n'=1-10, iso-$OC_3H_7$, $C_6H_5$, or $CH_2C_6H_5$; W1 is 0-6, provided that m1+w1≤8; and $D_1$ is H, Cl, Br, $C_1$-$C_4$ alkyl, $C_1$-$C_4$ alkoxy, $C_6H_5$, or $CH_2C_6H_5$, and
   (d) one or more polymerizable crosslinking agents,
   wherein the listed components and any additional polymerizable components add up to 100% by weight,
   wherein the intraocular lens material in a fully-hydrated state has: a glass transition temperature of less than 22° C., a refractive index of 1.55 or greater measured at 589 nm and at room temperature (23±2° C.), an equilibrium water content of less than 5.0% by weight at a temperature of from 16° C. to 45° C., a Young's modulus of less than 80 MPa, an elongation of at least 100%, a 100% secant modulus of less than 6.0 MPa, and a glistening resistance characterized by having no bright field microvacuoles and about 10 or less microvacuoles per viewing screen.

2. The intraocular lens material according to embodiment 1, wherein the intraocular lens material in the fully hydrated state is substantially free (preferably free of age-related degradation as measured by low surface light scattering of less than 30 CCT units (computer-compatible-tape units) after 10-years accelerated aging (90° C., 81 days in a Balanced Salt Solution, BSS, from Alcon).

3. The intraocular lens material according to embodiment 1 or 2, wherein the polymerizable composition comprises from about 15% to about 25% by weight of the hydrophilic monomer.

4. The intraocular lens material according to embodiment 1 or 2, wherein the polymerizable composition comprises from about 18% to about 22% by weight of the hydrophilic monomer.

5. The intraocular lens material according to any one of embodiments 1 to 4, wherein the hydrophilic monomer is hydroxyethylmethacrylate, hydroxyethylacrylate, N-hydroxyethylacrylamide, N,N-dimethylacrylamide, or a combination thereof.

6. The intraocular lens material according to any one of embodiments 1 to 5, wherein the hydrophilic monomer is hydroxyethylmethacrylate, hydroxyethylacrylate, or a combination thereof.

7. The intraocular lens material according to any one of embodiments 1 to 6, wherein the hydrophilic monomer is hydroxyethylmethacrylate.

8. The intraocular lens material according to any one of embodiments 1 to 7, wherein the polymerizable composition comprises from about 25% to about 75% by weight of said one or more poly(phenyl ether)-containing monomers of formula (I).
9. The intraocular lens material according to any one of embodiments 1 to 8, wherein wherein the polymerizable composition comprises from about 30% to about 65% by weight of said one or more poly(phenyl ether)-containing monomers of formula (I).
10. The intraocular lens material according to any one of embodiments 1 to 9, wherein in formula (I), $R_a$, $R_b$, $R_c$, $R_d$, $R_e$, $R_f$, $R_g$, $R_h$, and $R_i$ independent of one another are H.
11. The intraocular lens material according to any one of embodiments 1 to 10, wherein in formula (I), n1 is an integer from 2 to 6 (preferably an integer from 2 to 4, more preferably an integer 2 or 3).
12. The intraocular lens material according to any one of embodiments 1 to 11, wherein in formula (I), n2 is an integer from 0 to 4.
13. The intraocular lens material according to any one of embodiments 1 to 12, wherein said one or more poly (phenyl ether)-containing monomers of formula (I) are selected from the group consisting of:

acrylate; 2-(4-propylphenyl)ethyl methacrylate; 2-(4-(1-methylethyl)phenyl)ethyl acrylate; 2-(4-(1-methylethyl)phenyl)ethyl methacrylate; 2-(4-methoxyphenyl)ethyl acrylate; 2-(4-methoxyphenyl)ethyl methacrylate; 2-(4-cyclohexylphenyl)ethyl acrylate; 2-(4-cyclohexylphenyl) ethyl methacrylate; 2-(2-chlorophenyl)ethyl acrylate; 2-(2-chlorophenyl)ethyl methacrylate; 2-(3-chlorophenyl)ethyl acrylate; 2-(3-chlorophenyl)ethyl methacrylate; 2-(4-chlorophenyl)ethyl acrylate; 2-(4-chlorophenyl) ethyl methacrylate; 2-(4-bromophenyl)ethyl acrylate; 2-(4-bromophenyl)ethyl methacrylate; 2-(3-phenylphenyl)ethyl acrylate; 2-(3-phenylphenyl)ethyl methacrylate; 2-(4-phenylphenyl)ethyl acrylate; 2-(4-phenylphenyl) ethyl methacrylate; 2-(4-benzylphenyl)ethyl acrylate; 2-(4-benzylphenyl)ethyl methacrylate; 2-(phenylthio) ethyl acrylate; 2-(phenylthio)ethyl methacrylate; 2-benzyloxyethyl acrylate; 3-benzyloxypropyl acrylate; 2-benzyloxyethyl methacrylate; 3-benzyloxypropyl methacrylate; 2-[2-(benzyloxy)ethoxy]ethyl acrylate; 2-[2-(benzyloxy)ethoxy]ethyl methacrylate; or combinations thereof.
17. The intraocular lens material according to embodiment 16, wherein said one or more aryl acrylic monomers are:

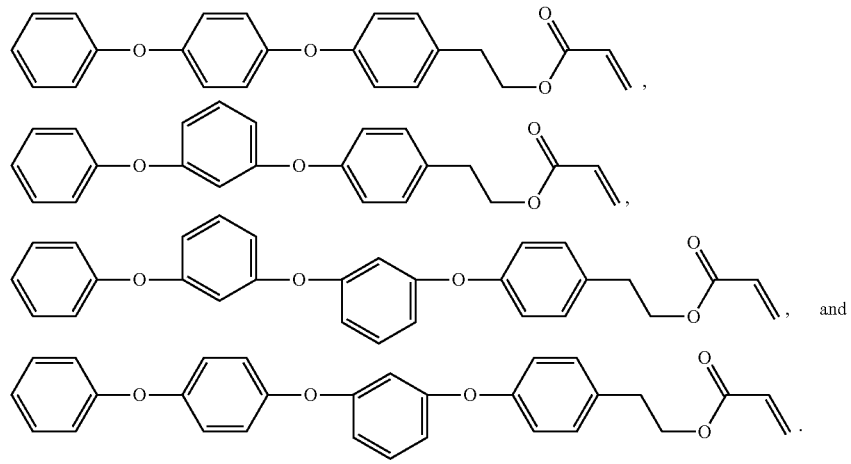

14. The intraocular lens material according to any one of embodiments 1 to 13, wherein the polymerizable composition comprises from about 10% to about 45% by weight of said one or more aryl acrylic monomers of formula (II).
15. The intraocular lens material according to any one of embodiments 1 to 14, wherein the polymerizable composition comprises from about 20% to about 40% by weight of said one or more aryl acrylic monomers of formula (II).
16. The intraocular lens material according to any one of embodiments 1 to 15, wherein said one or more aryl acrylic monomers are: 2-ethylphenoxy acrylate; 2-ethylphenoxy methacrylate; phenyl acrylate; phenyl methacrylate; benzyl acrylate; benzyl methacrylate; 2-phenylethyl acrylate; 2-phenylethyl methacrylate; 3-phenylpropyl acrylate; 3-phenylpropyl methacrylate; 4-phenylbutyl acrylate; 4-phenylbutyl methacrylate; 4-methylphenyl acrylate; 4-methylphenyl methacrylate; 4-methylbenzyl acrylate; 4-methylbenzyl methacrylate; 2-2-methylphenylethyl acrylate; 2,2-methylphenylethyl methacrylate; 2,3-methylphenylethyl acrylate; 2,3-methylphenylethyl methacrylate; 2,4-methylphenylethyl acrylate; 2,4-methylphenylethyl methacrylate; 2-(4-propylphenyl)ethyl 2-phenylethyl acrylate; 3-phenylpropyl acrylate; 4-phenylbutyl acrylate; 5-phenylpentyl acrylate; 2-benzyloxyethyl acrylate; 3-benzyloxypropyl acrylate; 2-[2-(benzyloxy)ethoxy]ethyl acrylate; their corresponding methacrylates, or combinations thereof.
18. The intraocular lens material of according to any one of embodiments 1 to 17, wherein the polymerizable composition comprises from about 1.0% to about 4.0% by weight of the polymerizable crosslinking agent.
19. The intraocular lens material of according to any one of embodiments 1 to 18, wherein the polymerizable composition comprises from about 1.2% to about 3.0% by weight of the polymerizable crosslinking agent.
20. The intraocular lens material of according to any one of embodiments 1 to 19, wherein the polymerizable composition comprises from about 1.5% to about 2.5% by weight of the polymerizable crosslinking agent.
21. The intraocular lens material according to any one of embodiments 1 to 20, wherein the polymerizable crosslinking agent is selected from the group consisting of: ethylene glycol dimethacrylate; diethylene glycol dimethacrylate; triethylene glycol dimethacrylate, tetraethylene glycol dimethacrylate, allyl methacrylate; 1,3-propanediol dimethacrylate; 2,3-propanediol dimethacrylate; 1,6-hexanediol dimethacrylate; 1,4-butanediol dimethacrylate; ethylene glycol diacrylate; diethylene glycol diacrylate; triethylene glycol diacrylate, tetraethylene glycol diacrylate, allyl acrylate; 1,3-propanediol diacrylate; 2,3-propanediol diacrylate; 1,6-hexanediol diacrylate; 1,4-butanediol diacrylate; N,N'-hexamethylene bisacrylamide; N,N'-hexamethylene bismethacrylamide; N,N'-dihydroxyethylene bisacrylamide; N,N'-dihydroxyethylene bismethacrylamide; N,N'-methylene bisacrylamide; N,N'-methylene bismethacrylamide; $CH_2=C(CH_3)C(=O)O-(CH_2CH_2O)_p-C(=O)C(CH_3)=CH_2$ where p=1-50; $CH_2=CHC(=O)O-(CH_2CH_2O)_p-C(=O)CH=CH_2$ where p=1-50; $CH_2=C(CH_3)C(=O)O(CH_2)_tO-C(CH_3)=CH_2$ where t=3-20; $CH_2=CHC(=O)O(CH_2)_tO-C(=O)CH=CH_2$ where t=3-20, and combinations thereof.

22. The intraocular lens material according to any one of embodiments 1 to 21, wherein the polymerizable cross-linking agent is selected from the group consisting of 1,6-hexanediol diacrylate, 1,4-butanediol diacrylate, N,N'-hexamethylene bisacrylamide, and combinations thereof.

23. The intraocular lens material according to any one of embodiments 1 to 22, wherein the intraocular lens material in the fully-hydrated state has a glass transition temperature of less than 17° C.

24. The intraocular lens material according to any one of embodiments 1 to 23, wherein the intraocular lens material in the fully-hydrated state has a glass transition temperature of less than 12° C.

25. The intraocular lens material according to any one of embodiments 1 to 24, wherein the intraocular lens material in the fully-hydrated state has an equilibrium water content of from about 1% to about 4.5% by weight at a temperature of from 16° C. to 45° C.

26. The intraocular lens material according to any one of embodiments 1 to 25, wherein the intraocular lens material in the fully-hydrated state has an equilibrium water content of from about 1.5% to about 4.0% by weight at a temperature of from 16° C. to 45° C.

27. The intraocular lens material according to any one of embodiments 1 to 26, wherein the intraocular lens material in the fully-hydrated state has a Young's modulus of from about 1 MPa to about 60 MPa.

28. The intraocular lens material according to any one of embodiments 1 to 27, wherein the intraocular lens material in the fully-hydrated state has a Young's modulus of from about 2.5 MPa to about 40 MPa.

29. The intraocular lens material according to any one of embodiments 1 to 28, wherein the intraocular lens material in the fully-hydrated state has a Young's modulus of from about 5 MPa to 20 MPa.

30. The intraocular lens material according to any one of embodiments 1 to 29, wherein the intraocular lens material in the fully-hydrated state has an elongation at break of at least 110%.

31. The intraocular lens material according to any one of embodiments 1 to 30, wherein the intraocular lens material in the fully-hydrated state has an elongation at break of at least at least 120%.

32. The intraocular lens material according to any one of embodiments 1 to 31, wherein the intraocular lens material in the fully-hydrated state has an elongation at break of at least 130%.

33. The intraocular lens material according to any one of embodiments 1 to 32, wherein the intraocular lens material in the fully-hydrated state has an elongation at break of from 130% to 300%.

34. The intraocular lens material according to any one of embodiments 1 to 33, wherein the intraocular lens material in the fully-hydrated state has a 100% secant modulus of about 4.5 MPa or less.

35. The intraocular lens material according to any one of embodiments 1 to 34, wherein the intraocular lens material in the fully-hydrated state has a 100% secant modulus of about 3.0 MPa or less.

36. The intraocular lens material according to any one of embodiments 1 to 35, wherein the polymerizable composition comprises a polymerizable UV-absorbing agent.

37. The intraocular lens material according to embodiment 36, wherein the polymerizable UV-absorbing agent is 2-(2H-benzo[d][1,2,3]triazol-2-yl)-4-methyl-6-(2-methylallyl)phenol, N-[2-[4-hydroxy-3-[2-(2-methylphenyl)diazenyl]phenyl]ethyl]methacryamide, or a combination thereof.

38. A wet-packed intraocular lens comprising or consisting essentially of an intraocular lens material according to any one of embodiments 1 to 37.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

Example 1

Materials
P4E3EA=2-{4-[3-(phenyloxy)phenoxy]phenyl}ethyl acrylate
DEGMBA=2-[2-(benzyloxy)ethoxy]ethyl acrylate
PEA=2-phenylethyl acrylate
HEMA=2-hydroxyethyl methacrylate
BDDA=1,4-butanediol diacrylate
TEGDMA=triethyleneglycol dimethacrylate
oMTP=2-(2H-benzo[d][1,2,3]triazol-2-yl)-4-methyl-6-(2-methyl)phenol
Blue blocker=N-[2-[4-hydroxy-3-[2-(2-methylphenyl)diazenyl]phenyl]ethyl]methacryamide
Irgacure 819=phenylbis(2,4,6-trimethylbenzoyl)phosphine oxide Microvacuole Testing SN60WF lenses were subjected to a 45° C.-21° C. ΔT dark-field microvacuole test. Samples are held at 45° C. for 48 hours in BSS and then removed to room temperature (~21° C.). After 2 hours samples are inspected under the Olympus BX60 microscope at ~250× magnification in dark-field mode. Each lens is evaluated in three different areas and the highest DF MVs are counted within the approximately 1000×1000 µm² imaging area.

Testing for the reproducibility studies were conducted a 45° C. to 37° C. AT bright-field microvacuole testing.

Surface Scatter and Bulk Haze Testing

In preparation for surface scatter and bulk haze testing lenses are placed in individual crimp-top vials filled with BSS under aseptic conditions. They are aged at 90° C. for 0, 40 and 81 days, which is equivalent to 0, 5 and 10 years at 35° C. Evaluation is made by Nidek EAS 1000 Scheimpflug.

A Scheimpflug image-capture system is set up for consistent surface-light-scattering (SLS) analysis of IOLs. A purpose-designed dark eye model is assembled that would hold the IOL being examined and that could be filled with air or with a balanced salt solution (BSS, Alcon Laboratories, Inc.) at room temperature. Images of the model eye and IOL are captured with an EAS-1000 Anterior Segment Analysis System (Nidek Co. Ltd.) using the following settings: 200 W flash, 10.00 mm slit length, 0.08 mm slit width, and a fixed camera angle position 45 degrees from the light beam path. Surface-light-scattering densitometry is measured in computer-compatible-tape (CCT) units ranging from 0 (least intense) to 255 (most intense). SLS densitometry values are measured for anterior surfaces and posterior surfaces of the IOL along the axis of a line that crosses perpendicular to the center of the IOL optic. Peak scatter intensities are measured for anterior surfaces and posterior surfaces along the axis of 3 lines within the central 3.0 mm optic zone, yielding 6 measurements per IOL, which are then averaged. Surface light scattering is measured with IOLs dry, wetted (after approximately 2 minutes in a balanced salt solution), and hydrated (after 24 hours in a balanced salt solution).

Tensile Testing

For the determination of tensile properties of resultant materials, 8-12 mini-dogbones were cut from slab samples of each material tested, hydrated in BSS in microcentrifuge vials, and equilibrated to 18° C. in a water bath. Temperature controlled tensile testing was carried out using the Biopuls environmental chamber, which was mounted on the Instron 5943 Material Tester. The Biopuls chamber was regulated to 18° C. via circulating temperature controlled water bath. Just prior to testing mini-dogbones were removed from the 18° C. water bath and placed in the crossheads of the tensile tester. The Biopuls chamber was raised over the crossheads and samples further equilibrated for 2-min in the Biopuls chamber. Mini-dogbones were pulled at 50 mm/min rate to the breaking point to measure the tensile properties. Tensile strength (ultimate tensile stress), elongation at break (maximum strain), and Young's and secant modulus values were determined from the average of 8-12 runs per material formulation.

Equilibrium Water Content

Following % extractables determination, the same samples were placed into glass vials, immersed in a Balanced Salt Solution (BSS, Alcon) and placed into a 35° C. water bath for at least 24 hours, then removed and re-weighed to determine % equilibrium water content (EWC). In a few cases the water content was determined by weighing samples before and after MV testing.

Glass Transition Temperature

The glass transition temperature (Tg) of materials in dry or fully-hydrated states was measured by differential scanning calorimetry at 5° C./minute, and was determined at the midpoint of the transition of the heat flux curve.

Refractive Index (RI)

The refractive index of the materials was measured using a Bausch & Lomb refractometer (Cat. #33.46.10) at 589 nm and 35° C. Test slab samples were hydrated in deionized water or BSS for a minimum of 24 hours, blotted dry, and then placed on the sample stage. Measurements were taken within 5 minutes of placing on stage.

Example 2

Synthesis of 3-(4-phenoxyphenoxy)phenol

To a 1 L round bottom flask were charged 4-phenoxyphenol (186 g, 1.0 mol), THF (150 mL), sodium hydroxide (48 g, 1.2 mol), and DI water (100 mL). The mixture was magnetically stirred at room temperature for one hour, followed by removal of solvent under reduced pressure. The white solid was then dried under vacuum (70 mTorr) at 150° C. overnight and cooled to room temperature. To the flask were then added 3-(benzyloxy)-1-bromobenzene (263 g, 1.0 mol) and anhydrous pyridine (150 mL). The mixture was purged with nitrogen for 15 min, followed by the addition of cuprous chloride (10 g, 0.1 mol). The mixture was then purge with nitrogen for additional 15 min and then sealed under nitrogen and magnetically stirred in a 130° C. oil bath for a week. After removal of pyridine under vacuum, the crude product was dissolved in methylene chloride (600 mL) and washed with 2N HCl (200 mL×3), 2N NaOH (200 mL×3). After removal of solvent under reduced pressure, the crude product was recrystallized from methanol/ethyl acetate (9/1, v/v). The product was then hydrogenated at 100 PSI in THF using palladium 10% on carbon as catalyst to give crude 3-(4-phenoxyphenoxy)phenol. This crude product was then distilled under vacuum to give the product as white crystals (200 g, 72% over two steps)

Synthesis of 2-{4-[3-(4-phenoxyphenoxy)phenoxy] phenyl}ethanol

To a 1 L round bottom flask were charged 3-(4-phenoxyphenoxy)phenol (167 g, 0.72 mol), THF (150 mL), sodium hydroxide (28.8 g, 0.72 mol), and DI water (100 mL). The mixture was magnetically stirred at room temperature for one hour, followed by removal of solvent under reduced pressure. The white solid was then dried under vacuum (70 mTorr) at 150° C. overnight and cooled to room temperature. To the flask were then added 1-bromo-4-[2-(phenylmethoxy)-ethyl]-benzene (197 g, 0.68 mol) and anhydrous pyridine (120 mL). The mixture was purged with nitrogen for 15 min, followed by the addition of cuprous chloride (15 g, 0.15 mol). The mixture was then purge with nitrogen for additional 15 min and then sealed under nitrogen and magnetically stirred in a 130° C. oil bath for a week. After removal of pyridine under vacuum, the crude product was dissolved in methylene chloride (600 mL) and washed with 2N HCl (200 mL×3), 2N NaOH (200 mL×3). After removal of solvent under reduced pressure, the crude product was recrystallized from methanol. The product was then hydrogenated at 100 PSI in THF using palladium 10% on carbon as catalyst to give crude 2-(4-(4-phenoxyphenoxy)phenyl] ethanol. This crude product was then distilled under vacuum followed by recrystallization from hexanes/ethyl acetate (9/1, v/v) to give the product as white crystals (158 g, 66% over two steps).

Synthesis of 2-{4-[3-(4-phenoxyphenoxy)phenoxy] phenyl}ethyl acrylate (P4E3EA)

To a 1 L threeneck round bottom flask equipped with mechanical stirrer were charged 2-{4-[3-(4-phenoxyphenoxy)phenoxy]phenyl}ethanol (158 g, 0.41 mol), anhydrous triethylamine (100 mL, 0.70 mol), and anhydrous methylene chloride (500 mL). The solution was cooled in an ice/salt bath under dry air blanket for 15 mins. Acryloyl chloride (44 mL, 0.54 mol) was added into the vigorously stirred cold solution through an addition funnel over 90 min and the addition rate was adjusted to keep the temperature of the reaction mixture below 10° C. After the addition, the reaction mixture was stirred in the ice/salt bath for additional two hours followed by quenching with the addition of 2M HCl (300 mL). The mixture was extracted with ethyl acetate (300 mL×3) and the combined organic layer was washed with DI water (200 mL×3), aqueous sodium bicarbonate (200 mL×2), and dried over MgS04. Filtration and removal of solvents under reduced pressure gave the crude product as light brown oil which was purified on silica gel using Hexanesimethylene chloride (3/2, v/v) as eluent to give P4E3EA as a white solid (144 g, 81%).

Example 3

Synthesis of 2-[2-(Benzyloxy)ethoxy]ethyl acrylate (DEGMBA)

To a 1 L three-neck round bottom flask equipped with mechanical stirrer were charged diethylene glycol monobenzyl ether (98.0 g, 0.5 mol), anhydrous triethylamine (120 mL, 0.85 mol), and anhydrous THF (300 mL). The solution was cooled in an ice/salt bath under dry air blanket for 15 minutes. Acryloyl chloride (55 mL, 0.68 mol) was added into the vigorously stirred cold solution through an addition funnel over 90 minutes and the addition rate was adjusted to keep the temperature of the reaction mixture below 10° C. After the addition, the reaction mixture was stirred in the ice/salt bath for additional two hours followed by quenching with the addition of 2M HCl (400 mL). The mixture was extracted with ethyl acetate (300 mL×3) and the combined organic layer was washed with DI water (200 mL×3), aqueous sodium bicarbonate (200 mL×2), and dried over MgSO$_4$. Filtration and removal of solvents under reduced pressure gave the crude product as light brown oil which was purified on silica gel using Hexanes/Ethyl acetate (4/1, v/v) as eluent to give the final product as a colorless oil (105.0 g, 0.42 mol, yield: 84%).

Example 4

Crosslinked Polymers

The monomers from Examples 2 and 3 were formulated as shown in Table 1. Test samples measuring 0.9 mm in thickness were blue light cured at 55° C. for 1 hour. Samples were extracted in acetone for 20 hours at room temperature and then dried slowly at ambient temperature for 20 hours, followed by vacuum (0.1 mm Hg) for a minimum of 20 hours at 70° C.

TABLE 1

| Component | SAMPLE (% w/w) | | | | |
| --- | --- | --- | --- | --- | --- |
| | 54B | 54D | 54E | 54F | 54G |
| P4E3EA | 56.13 | 51.22 | 50.60 | 41.55 | 41.97 |
| DEGMBA | — | 24.85 | — | 34.93 | 34.99 |
| HEMA | 30.01 | 19.90 | 20.06 | 19.97 | 20.00 |
| PEA | 9.98 | — | 25.02 | — | — |
| BDDA | 0.99 | 2.20 | 2.49 | 1.69 | 1.20 |
| TEGDMA | 1.03 | — | — | — | — |
| oMTP | 1.81 | 1.79 | 1.79 | 1.81 | 1.80 |
| Blue Blocker | 0.04 | 0.04 | 0.04 | 0.04 | 0.04 |
| Irgacure 819 | 0.31 | 0.30 | 0.30 | 0.30 | 0.30 |

The samples prepared above were hydrated in a water bath at 23° C. and the % EWC (equilibrium water content) and refractive index were determined at 23° C.

The tensile properties of the samples prepared above were also evaluated at 19° C. using hydrated test samples as follows. Tensile bar specimens in the fashion of "dogbones" were cut from each sample group using a die and press. Typically 3 specimens per slab were prepared and 9 total specimens per formulation. Tensile properties were measured using an Instron 5543 extensometer at 500 mm/min crosshead speed. Stress at break, % strain at break, Young's modulus, and 100% secant modulus data were obtained.

Glistening resistance was determined by placing three lenses of each formulation into 20-mL vials containing about 20 mL deionized water and incubating them in a waterbath at 45° C. for 24 hours. The sample vials were removed from the water bath and placed on the lab bench to cool to room temperature (typically 23-24° C.). After cooling to room temperature, each lens was imaged using an Olympus BX60 microscope under bright field (BF) and dark field (DFA) settings at 10 times with a 2 times magnifier.

The weight percentage of extactables was determined as follows. Three-five polymer slabs of each cured formulation were weighed for % extractables. The polymer slabs were extracted in acetone for at least 16 hours at ambient temperature with one solvent change out after the first hour, and then allowed to dry while covered with aluminum foil at ambient temperature for 8 hours. Slabs were further dried under reduced atmosphere at 60° C. for at least 16 hours. Slabs were removed and cooled to room temperature (23° C.). Previously weighed slabs were weighed again for % extractables.

The results are reported in Table 2.

TABLE 2

| | Sample ID | | | |
| --- | --- | --- | --- | --- |
| | 54D | 54E | 54F | 54G |
| % Extractables (N = 12) | 1.2 | 1.3 | 2.1 | 2.8 |
| EWC (%) | 2.4 | — | 3.1 | 3.2 |
| R.I. at 589 nm (hydrated) | 1.566 | — | 1.556 | 1.556 |
| Young's Modulus (MPa) | 76.3 ± 7.4 | — | 16.3 ± 3.5 | — |
| Strain at Break (%) | 147 ± 10.3 | — | 135.9 ± 11.1 | — |
| 100% Secant Modulus (MPa) | 3.05 ± 0.09 | — | 1.26 ± 0.02 | — |
| Tg (° C., dry) | 17.1 | 30.5 | 8.5 | — |
| Tg (° C., hydrated) | 8.0 | 21.3 | −1.8 | — |

We claim:
1. A polymeric intraocular lens material, which is polymerization product of a polymerizable composition comprising
(a) from about 10% to about 30% by weight of a hydrophilic monomer relative to the total amount of all polymerizable components, wherein the hydrophilic monomer is hydroxyethylmethacrylate, hydroxyethylacrylate, N-hydroxyethylmethacrylamide, N-hydroxyethylacrylamide, N,N-dimethylacrylamide, N,N-dimethylmethacrylamide, or a combination thereof,
(b) from about 20% to about 85% by weight of one or more poly(phenyl ether)-containing monomers of formula (I) relative to the total amount of all polymerizable components

(I)

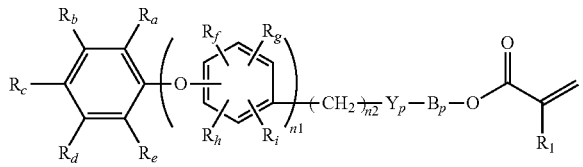

wherein:

$R_1$ is H or $CH_3$;

$R_a$, $R_b$, $R_c$, $R_d$, $R_e$, $R_f$, $R_g$, $R_h$, and $R_i$ independent of one another are H, $C_1$-$C_{12}$ alkyl, or $C_1$-$C_{12}$ alkoxy;

$B_p$ is a direct bond, $(CH_2)_{m1}$, or $(OCH_2CH_2)_{m2}$, in which m1 is 2-6 and m2 is 1-10;

n1 is an integer from 1 to 9;

n2 is an integer from 0 to 6;

$Y_p$ is a direct bond, O, S, OC(=O)NH, NHC(=O)NH, or NR' in which R' is H, $C_1$-$C_{10}$ alkyl, $C_6H_5$, or $CH_2C_6H_5$, (c) from 0 to about 50% by weight of one or more aryl acrylic monomers of formula (II) relative to the total amount of all polymerizable components

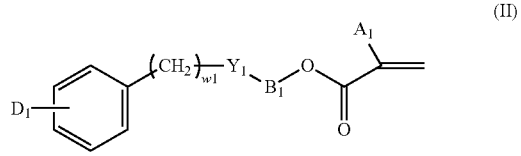

(II)

wherein $A_1$ is H or $CH_3$; $B_1$ is $(CH_2)_{m1}$ or $[O(CH_2)_2]_{z1}$ in which m1 is 2-6 and z1 is 1-10; $Y_1$ is a direct bond, O, S, or NR" in which R" is H, $CH_3$, $C_{n'}H_{2n'+1}$ in which n'=1-10, iso-$OC_3H_7$, $C_6H_5$, or $CH_2C_6H_5$; W1 is 0-6, provided that m1+w1≤8;

and $D_1$ is H, Cl, Br, $C_1$-$C_4$ alkyl, $C_1$-$C_4$ alkoxy, $C_6H_5$, or $CH_2C_6H_5$, and (d) one or more polymerizable crosslinking agents, wherein the listed components and any additional polymerizable components add up to 100% by weight, wherein the intraocular lens material in a fully-hydrated state has: a glass transition temperature of less than 22° C., a refractive index of 1.55 or greater measured at 589 nm and at room temperature (23±2° C.), an equilibrium water content of less than 5.0% by weight at a temperature of from 16° C. to 45° C., a Young's modulus of less than 80 MPa, an elongation of at least 100%, a 100% secant modulus of less than 6.0 MPa, and a glistening resistance characterized by having no bright field microvacuoles and about 10 or less microvacuoles per viewing screen.

2. The intraocular lens material of claim 1, wherein the intraocular lens material in the fully hydrated state has a surface light scattering of less than 30 CCT units (computer-compatible-tape units) after 10-years accelerated aging (90° C., 81 days in a Balanced Salt Solution, BSS).

3. The intraocular lens material according to claim 2, wherein the polymerizable composition comprises from about 15% to about 25% by weight of the hydrophilic monomer.

4. The intraocular lens material according to claim 2, wherein the polymerizable composition comprises from about 25% to about 75% by weight of said one or more poly(phenyl ether)-containing monomers of formula (I).

5. The intraocular lens material according to claim 2, wherein the polymerizable composition comprises from about 10% to about 45% by weight of said one or more aryl acrylic monomers of formula (II).

6. The intraocular lens material of according to claim 2, wherein the polymerizable composition comprises from about 1.0% to about 4.0% by weight of the polymerizable crosslinking agent.

7. The intraocular lens material according to claim 2, wherein in formula (I), $R_a$, $R_b$, $R_c$, $R_d$, $R_e$, $R_f$, $R_g$, $R_h$, and $R_i$ independent of one another are H, n1 is an integer from 2 to 6, n2 is an integer from 0 to 4.

8. The intraocular lens material of claim 2, wherein said one or more poly(phenyl ether)-containing monomers of formula (I) are selected from the group consisting of:

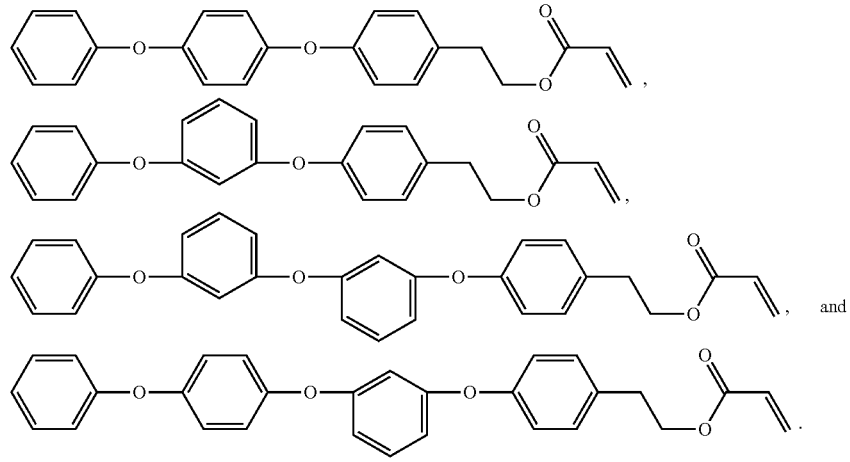

9. The intraocular lens material of claim 2, wherein said one or more aryl acrylic monomers are: 2-ethylphenoxy acrylate; 2-ethylphenoxy methacrylate; phenyl acrylate; phenyl methacrylate; benzyl acrylate; benzyl methacrylate; 2-phenylethyl acrylate; 2-phenylethyl methacrylate; 3-phenylpropyl acrylate; 3-phenylpropyl methacrylate; 4-phenylbutyl acrylate; 4-phenylbutyl methacrylate; 4-methylphenyl acrylate; 4-methylphenyl methacrylate; 4-methylbenzyl acrylate; 4-methylbenzyl methacrylate; 2-2-methylphenylethyl acrylate; 2,2-methylphenylethyl methacrylate; 2,3-methylphenylethyl acrylate; 2,3-methylphenylethyl methacrylate; 2,4-methylphenylethyl acrylate; 2,4-methylphenylethyl methacrylate; 2-(4-propylphenyl)ethyl acrylate; 2-(4-propylphenyl)ethyl methacrylate; 2-(4-(1-methylethyl)phenyl)ethyl acrylate; 2-(4-(1-methylethyl)phenyl)ethyl methacrylate; 2-(4-methoxyphenyl)ethyl acrylate; 2-(4-methoxyphenyl)ethyl methacrylate; 2-(4-cyclohexylphenyl)ethyl acrylate; 2-(4-cyclohexylphenyl)ethyl methacrylate; 2-(2-chlorophenyl)ethyl acrylate; 2-(2- chlorophenyl)ethyl methacrylate; 2-(3-chlorophenyl)ethyl acrylate; 2-(3-chlorophenyl)ethyl methacrylate; 2-(4-chlorophenyl)ethyl acrylate; 2-(4-chlorophenyl)ethyl methacrylate; 2-(4-bromophenyl)ethyl acrylate; 2-(4-bromophenyl) ethyl methacrylate; 2-(3-phenylphenyl)ethyl acrylate; 2-(3-phenylphenyl)ethyl methacrylate; 2-(4-phenylphenyl)ethyl acrylate; 2-(4-phenylphenyl)ethyl methacrylate; 2-(4-benzylphenyl)ethyl acrylate; 2-(4-benzylphenyl)ethyl methacrylate; 2-(phenylthio)ethyl acrylate; 2-(phenylthio)ethyl methacrylate; 2-benzyloxyethyl acrylate; 3-benzyloxypropyl acrylate; 2-benzyloxyethyl methacrylate; 3-benzyloxypropyl methacrylate; 2-[2-(benzyloxy)ethoxy]ethyl acrylate; 2-[2-(benzyloxy)ethoxy]ethyl methacrylate; or combinations thereof.

10. The intraocular lens material of claim 2, wherein said one or more aryl acrylic monomers are: 2-phenylethyl acrylate; 3-phenylpropyl acrylate; 4-phenylbutyl acrylate; 5-phenylpentyl acrylate; 2-benzyloxyethyl acrylate; 3-benzyloxypropyl acrylate; 2-[2-(benzyloxy)ethoxy]ethyl acrylate; their corresponding methacrylates, or combinations thereof.

11. The intraocular lens material of claim 2, wherein the polymerizable crosslinking agents are selected from the group consisting of ethylene glycol dimethacrylate; diethylene glycol dimethacrylate; triethylene glycol dimethacrylate, tetraethylene glycol dimethacrylate, allyl methacrylate; 1,3-propanediol dimethacrylate; 2,3-propanediol dimethacrylate; 1,6-hexanediol dimethacrylate; 1,4-butanediol dimethacrylate; ethylene glycol diacrylate; diethylene glycol diacrylate; triethylene glycol diacrylate, tetraethylene glycol diacrylate, allyl acrylate; 1,3-propanediol diacrylate; 2,3-propanediol diacrylate; 1,6-hexanediol diacrylate; 1,4-butanediol diacrylate; N,N'-hexamethylene bisacrylamide; N,N'-hexamethylene bismethacrylamide; N,N'-dihydroxyethylene bisacrylamide; N,N'-dihydroxyethylene bismethacrylamide; N,N'-methylene bisacrylamide; N,N'-methylene bismethacrylamide; $CH_2=C(CH_3)C(=O)O-(CH_2CH_2O)_p-C(=O)C(CH_3)=CH_2$ where p=1-50; $CH_2=CHC(=O)O-(CH_2CH_2O)_p-C(=O)CH=CH_2$ where p=1-50; $CH_2=C(CH_3)C(=O)O(CH_2)_tO-C(CH_3)=CH_2$ where t=3-20; $CH_2=CHC(=O)O(CH_2)_tO-C(=O)CH=CH_2$ where t=3-20, and combinations thereof.

12. The intraocular lens material of claim 11, wherein the polymerizable crosslinking agents are selected from the group consisting of 1,6-hexanediol diacrylate, 1,4-butanediol diacrylate, N,N'-hexamethylene bisacrylamide, and combinations thereof.

13. The intraocular lens material of claim 2, wherein the polymerizable composition comprises a polymerizable UV-absorbing agent.

14. The intraocular lens material of claim 13, wherein the polymerizable UV-absorbing agent is 2-(2H-benzo[d][1,2,3]triazol-2-yl)-4-methyl-6-(2-methylallyl)phenol, N-[2-[4-hydroxy-3-[2-(2-methylphenyl)diazenyl]phenyl]ethyl] methacryamide, or a combination thereof.

15. The intraocular lens material claim 2, wherein the hydrophilic monomer is hydroxyethylmethacrylate, hydroxyethylacrylate, N-hydroxyethylacrylamide, N,N-dimethylacrylamide, or a combination thereof.

16. The intraocular lens material of claim 2, wherein the hydrophilic monomer is hydroxyethylmethacrylate, hydroxyethylacrylate, or a combination thereof.

17. The intraocular lens material of claim 2, wherein the hydrophilic monomer is hydroxyethylmethacrylate.

18. The intraocular lens material of claim 2, wherein the intraocular lens material in the fully-hydrated state has at least one property selected from the group consisting of: a glass transition temperature of less than 17° C.; an equilibrium water content of from about 1% to about 4.5% by weight at a temperature of from 16° C. to 45° C.; a Young's modulus of from about 1 MPa to about 60 MPa; an elongation at break of at least 110%; a 100% secant modulus of about 4.5 MPa or less; and combinations thereof.

19. The intraocular lens material of claim 2, wherein the intraocular lens material in the fully-hydrated state has a glass transition temperature of less than 12° C.; an equilibrium water content of from about 1.5% to about 4.0% by weight at a temperature of from 16° C. to 45° C.; a Young's modulus of from about 5 MPa to 20 MPa; an elongation at break of from 130% to 300%; a 100% secant modulus of about 3.0 MPa or less; and combinations thereof.

20. A wet-pack intraocular lens comprising or consisting essentially of an intraocular lens material of claim 2.

* * * * *